United States Patent [19]

Weisberg

[11] Patent Number: 4,840,914

[45] Date of Patent: Jun. 20, 1989

[54] GENDER-INDICATING COLORMETRIC TEST ON PREGNANCY URINE AND TEST KIT THEREFOR

[76] Inventor: Kenneth Weisberg, 606 St. Andrews Rd., Hollywood, Fla. 33021

[21] Appl. No.: 248,909

[22] Filed: Sep. 26, 1988

[51] Int. Cl.$^4$ ............................................. G01N 33/52
[52] U.S. Cl. ..................................... 436/183; 422/61; 436/65
[58] Field of Search ................. 436/536, 65, 814, 183; 422/61

[56] References Cited

FOREIGN PATENT DOCUMENTS 801719 8/1980 World Int. Prop. O. .

*Primary Examiner*—Barry S. Richman
*Assistant Examiner*—Marcella Fruchter
*Attorney, Agent, or Firm*—Herbert L. Lerner; Laurence A. Greenberg

[57] ABSTRACT

A gender-indicating test of the unborn child is provided. It is a colorimetric test on the pregnancy urine performed on samples obtained after about the 20th week of the pregnancy. The gender-indicating composition for use in the test is a mixture of alkali hydroxide and metallic aluminum. The colored results of the exothermic reaction of the composition with the urine is evaluated—tan solutions indicate a female child and brown solutions indicate a male child. The invention includes the method, the compositions used in the method and a convenient kit containing the subdivided composition in test units for performing the gender-indicating test.

9 Claims, No Drawings

GENDER-INDICATING COLORMETRIC TEST ON PREGNANCY URINE AND TEST KIT THEREFOR

FIELD OF THE INVENTION

This invention relates to a method and a kit for determining the gender of the unborn fetus and more particularly to a test for ascertaining the gender of the baby in the womb based upon tests on the pregnancy urine.

BACKGROUND OF THE INVENTION

The fascination of guessing the sex of the unborn baby in the womb is deeply ingrained in all cultures. Various folklore techniques have been used. They have ranged from torque on suspended wedding rings to color reflections from flowers, coins held near the belly or colors transmitted through various unguents applied to the belly. The shape of the belly was also a sure indicator—round could be either a boy or a girl depending on the specific culture. Needless to say, the prognosticators were either right or wrong—usually about half the time. None of the methods were scientifically based.

Recently some methods based on science have had favor based to some degree upon endocrinology. Acne-like complexion changes in the mother have been held to indicate a probable girl. These are based upon supposed excesses of female hormones. Improvement in the mother's complexion was suggestive of a probable boy. The reasoning was a supposed neutralization of any excessive female hormones by the male hormones from the boy fetus.

There may be some basis to this method as statistically, some doctors who have followed up their original predictions claim improved guessing averages. However, recent improvements in hormone assays in the blood of pregnant women have not shown any significant alteration in specific hormone levels between women carrying boys and women carrying girls.

Sure methods exist for determining the sex of the fetus, but they are invasive of the womb or fetus to some degree. Amniocentesis involves insertion of a cannula or needle into the amniotic sac. In the hands of a skilled practitioner who follows the fetal position with various visualization aids, there is little danger, but such dangers do exist either from contact between the fetus and the sampling needle or from the action upon the fetus of the ultrasound or x-ray visualization aids.

Another direct method involves visualization of the genitalia by following the fetus with ultra-sound wands until the fetus and the transducer are properly positioned to provide an image of the fetal genitalia on the ultra-sound monitor. The effect of subjecting the fetus to ultra-sound is controversial.

THE INVENTION

The present invention is based upon tests performed on the urine of the pregnant mother and thus is neither invasive of the pregnant uterus nor requires any direct contact with the pregnant belly with concomitant risks.

Pregnancy urine is regularly submitted to her obstetrician by the pregnant mother-to-be. In the past these samples, preferably from the first voiding in the morning, are brought to the doctor for routine urine analysis for pregnancy complications that are indicated by proteinuria.

The present invention is directed to tests performed on these samples of pregnancy urine preferably from the first voiding in the morning submitted during the prenatal visits. The tests of this invention, routinely performed in the doctor's office, provide a reliable indication of the gender of the soon to be born child. The tests on the urine involve no further contact with either the mother or the child and thus are completely without danger to either. The test is performed only on the urine sample and has been found to be accurate if performed upon the urine voided after about the twentieth week of the pregnancy, but preferably after the twenty-fourth week. The accepted full term for a normal pregnancy is 39 to 40 weeks. Tests performed before about the twentieth week are often ambiguous or wrong but tests performed after the twenty-fourth week of the pregnancy have had a high degree of accuracy in gender prediction. Accuracy, of course, is determined upon birth.

Basically this invention provides a method for determining the gender of the unborn child and comprises contacting the pregnancy urine from the mother with a gender-indicating composition, initiating a chemical reaction between the urine sample and the components of the gender-indicating composition, then comparing the color formed as a result of this reaction with standards indicating the sex or gender of the fetus in the mother's womb. As mentioned, the urine sample is preferably from the first voiding of any day after about the twentieth week of the pregnancy and preferably after about the twenty-fourth week.

The gender-indicating composition comprises a mixture of an alkali-hydroxide and metallic aluminum particles. The mixture components can react between themselves but only function properly in this invention when they react in the presence of pregnancy urine as the reaction medium and as an additional component. Thus it is preferred to keep the hydroxide and metallic aluminum particles in dry state. When dry, they do not react and the dry mixture, with the access to water vapor minimized in closed container# has a shelf-life of at least, six months.

The dry mixture of commercially available alkali hydroxide prills and reagent-grade aluminum turnings is added to the urine specimen.

The water in the urine wets the dry mixture and initiates a reaction between them and with the various pregnancy-caused components of the pregnancy urine. The reaction between the aluminum and the alkali hydroxide, when wetted, is vigorously exothermic and emits hydrogen. The heat, the reaction products such as the alkali aluminates, the hydrogen etc., react with the dissolved urine components including some excreted gender—indicating compounds and form colored products in the reaction medium. The color of the resultant reacted specimen is indicative of the sex of the fetus.

Tan solutions indicate a female fetus and darker or brownish solutions indicate a male fetus. The color is observed after the exothermic reaction is completed and the heating and vigorous mixing cease.

DETAILED DESCRIPTION OF THE INVENTION

The pregnancy urine used for the test needs no special storage precaution except that it be transferred to well cleaned bottles after voiding. Preferably the urine from the first voiding should be used although the test is usually successful on later urines. The urine should be preferably tested after the twentieth week of the pregnancy. In a series of tests upon unknown samples the method of the invention has been found to be 80 to 90% accurate on specimens from the 20th to 24th week of the pregnancy and between 95 and 100% accurate on specimens obtained after the 24th week.

Inaccuracies of the sex-prediction by the method of this invention have been found to be caused by insufficient amounts of urine used in the test, by adding a partially reacted mixture to the urine, use of urine obtained before the twentieth week, excess hematuria or proteinuria which interfere with the color of the sample.

The gender-indicating composition of this invention can be freshly mixed before introduction into the specimen or may be premixed and held under substantially low moisture conditions until use. Absolute anhydrous conditions need not be met as the components may be mixed in low humidity conditions, less than 40% relative humidity, filled into closed containers and held until ready for measuring and subdividing into portions for the test. The mixture may also be subdivided into portions and sealed into vials, bottles or plastic packets. Such subdivided portions, each sufficient for individual tests or for multiple tests have good shelf-life—i.e. at least six months but selected vials have performed accurately after about a year of dry storage.

The premixed composition should preferably contain about 3 parts hydroxide to each part of aluminum. The ratios may vary from 10 parts to one to 2 parts to one but the three to one ratio provides the clearest indication of gender.

The alkali hydroxide may be either sodium or potassium hydroxide in the form of compressed prills, compacts or granules. They are both commercially available in such forms having an approximate particle diameter of a fiftieth to a quarter inch. Such granules or prills are preferred as they do not react too rapidly. Powders cause the specimen to boil out of the test tube. Larger sizes cause segregation of the admixed aluminum particles which may lead to improper proportions of reactants.

The other alkali hydroxides may be used but the cost of Lithium or Rubidium is prohibitive and offers no advantage. Calcium and magnesium hydroxides are not useful as they are not sufficiently reactive with the aluminum.

The aluminum metal is preferably used in the form of crimped ribbon or turnings as are commercially available as metallic aluminum, laboratory grade. The aluminum powders are to be avoided as they are often pyrophoric in the air. They also react too vigorously with the urine and hydroxide and may initiate explosions with the emitted hydrogen.

When used in the indicated particle sizes and in the proportions recommended, the pre-mixtures of the components are useful and can form articles of commerce for the practice of this invention.

As such, the mixture of ingredients in subdivided form for individual specimen testing is novel and is useful for the practice of the invention. Thus it forms a distinct part thereof. The mixture of components for the practice of the invention is used in a ratio from 1:1 to about 1:6 (ounces weight of the gender indicating composition to ounces volume of the specimen), but for practical purposes, a ratio of 1:2 is preferred.

When the composition is added to the urine, an exothermic reaction takes place with much circulation of the solids in the urine. The reaction subsides after a time and the color of the resultant solution is observed A tan color identifies a female fetus. The tan shades are of various depths and intensities and are best viewed against a white paper as a background. A brown color identifies a male fetus. The intensity of the brown color, indicating a male, is characteristic and cannot be confused with the tan color indicating a female. The difference in colors can be accentuated by the use of blue-tinted sodium hydroxide pellets, which is commercially tinted as a safety precaution. Various laboratory supply houses furnish such tinted NaOH in Reagent Grades. The blue tint has no effect on the tan shades but intensifies the brown shades.

Testing of the composition for specificity shows that when mixed with male or non-pregnant female urine, the color of the urine is the normal yellow—neither tan or brown.

The exact nature of the cause of the gender-indicating color has not been identified but search of the literature indicates that it is not caused by excess excretion of either male or female hormone in the urine. Assays of urine show no hormone differentiation in the urine until just about term, when a large amount of progesterone is excreted to initiate labor.

The source of the color differences may be caused by the postulated releases of pituitary hormones including various protogonadotropic hormones, many of which are only now being recognized. However, while the exact cause of the color difference is not yet understood nor are the reactions of the urine components with composition presently characterized, the accuracy of the test in predicting the gender of the baby is clear.

EXAMPLES

The invention will be illustrated by the presently preferred procedure where an ounce of urine, by volume, is introduced into a 90 ml test tube. A half ounce by weight of the test composition, previously subdivided into a test unit into a plastic capped vial, is introduced into the urine in the test tube.

The reaction is self-initiating and proceeds rapidly to completion indicated by lack of evolution of gas and the end of the resulting agitation. The color of the quiet solution is judged by viewing against a white background, preferably a sheet of white paper. As mentioned, tan solutions indicate a female fetus; and brown solutions indicate a male fetus.

Since the samples for testing in the series varied in size, often insufficient samples were submitted. Often the test results were correct even when as little as half an ounce of urine by volume was used to half an ounce by weight of the reagent mixture that is the claimed gender-indicating composition. However, these tests were not consistent.

Another source of inconsistency in the test series was the use of urines from women that were pregnant for less than about 20 weeks. After 20 weeks the results were more consistent and were substantially correct in all instances on adequate urine samples tested after 24 weeks of pregnancy.

The Table below is a schedule of urines tested from different patients, the duration of the pregnancy at time of the test, the predicted sex of the baby and the actual sex of the baby at birth. Where the test indication departed from the criteria noted above, the comments supply the reason for the departure and are based on the notes by the tester at the time of the test.

| Patient | Age | Week Tested | Result of Test | Birth Result | Test | Remarks |
|---|---|---|---|---|---|---|
| 1 | 20 | 38th | F | F | + | |
| 2 | 19 | 39th | M | M | + | |
| 3 | 26 | 41st | F | F | + | |
| 4 | 26 | 37th | M | M | + | |
| 5 | 24 | 29th | M | M | + | |
| 6 | 28 | 40th | F | M | − | Insuf. Specimen |
| 7 | 28 | 38th | M | M | + | |
| 8 | 33 | 38th | F | F | + | |
| 9 | 23 | 38th | F | F | + | |
| 10 | 23 | 39th | F | F | + | |
| 11 | 35 | 20th | M | F | − | Too Early |
| 12 | 27 | 34th | F | F | + | |
| 13 | 38 | 37th | M | M | + | |
| 14 | 29 | 31st | M | M | + | |
| 15 | 19 | 36th | F | M | − | Insuf. Specimen |
| 16 | 34 | 33rd | M | M | + | |
| 17 | 26 | 39th | F | F | + | |
| 18 | 29 | 32nd | F | F | + | |
| 19 | 33 | 32nd | M | M | + | ½ oz. Specimen |
| 20 | 22 | 32nd | F | M | − | Insuf. Specimen |
| 21 | 28 | 20th | F | F | + | Early in Term |
| 22 | 34 | 28th | F | F | + | |
| 23 | 28 | 40th | F | F | + | |
| 24 | 28 | 40th | M | M | + | |
| 25 | 26 | 19th | F | F | + | Early in Term |
| 26 | 25 | 32nd | F | F | + | ½ oz. Specimen |
| 27 | 22 | 15th | M | F | − | Insuf. Specimen Too Early |
| 28 | 20 | 30th | F | F | + | ½ oz. Specimen |
| 29 | 27 | 29th | F | F | + | |
| 30 | 25 | 20th | F | F | + | |
| 31 | 25 | 29th | F | F | + | |
| 32 | 34 | 24th | F | F | + | ½ oz. Specimen |
| 33 | 28 | 23rd | M | F | − | Insuf. Specimen |
| 34 | 26 | 37th | F | F | + | |
| 35 | 29 | 31st | F | F | + | |
| 36 | 24 | 18th | F | F | + | Early in Term |
| 37 | 26 | 26th | M | M | + | |
| 38 | 25 | 33rd | M | M | + | |
| 39 | 26 | 36th | M | M | + | |
| 40 | 34 | 32nd | F | F | + | |
| 41 | 22 | 35th | M | M | + | ½ oz. Specimen |
| 42 | 27 | 26th | M | M | + | |
| 43 | 25 | 32nd | M | M | + | |
| 44 | 32 | 33rd | M | M | + | |
| 45 | 31 | 22nd | M | F | − | Too Early |
| 46 | 38 | 36th | F | F | + | |
| 47 | 24 | 35th | F | F | + | |
| 48 | 31 | 28th | F | F | + | |
| 49 | 33 | 30th | M | M | + | ½ oz. Specimen |
| 50 | 28 | 38th | M | M | + | |
| 51 | 27 | 32nd | F | F | + | ½ oz. Specimen |
| 52 | 25 | 39th | M | M | + | |
| 53 | 32 | 33rd | F | M | − | Insuf. Specimen |
| 54 | 27 | 30th | F | F | + | |
| 55 | 28 | 33rd | F | F | + | |
| 56 | 28 | 30th | M | M | + | |
| 57 | 28 | 16th | F | F | + | Early in Term |
| 58 | 27 | 36th | F | F | + | |
| 59 | 27 | 28th | M | M | + | |
| 60 | 18 | 28th | F | F | + | ½ oz. Specimen |
| 61 | 28 | 20th | M | F | − | Test too Early |
| 62 | 27 | 33rd | F | F | + | |
| 63 | 27 | 33rd | F | F | + | |
| 64 | 20 | 27th | M | M | + | |
| 65 | 27 | 28th | M | M | + | ½ oz. Specimen |
| 66 | 31 | 34th | F | F | + | |
| 67 | 24 | 19th | F | M | − | Too Early Insuf. Specimen |
| 68 | 27 | 36th | M | M | + | |
| 69 | 31 | 34th | M | M | + | |
| 70 | 27 | 39th | M | M | + | |

The method of invention has been described in its presently preferred form but it is envisioned that it may be practiced in other amounts and in other reaction vessels. The automation of the tests is possible whereby the urine samples may be smaller and the composition is added in smaller but aliquot amounts. The automation of the test, as an aspect of automated urine-analysis is also within the scope of the practice of the invention.

Also within the scope of the invention is the addition of the gender-indicating composition to the urine by the seriation introduction of its components. To the urine in the test tube, is first added, the proper amount of alkali hydroxide and then the aluminum metal.

Also within the scope of the invention is the reversal of the order of addition of the components. Another variation possible, when the components are individually added, is the use of the alkali hydroxide in concentrated solution. There are commercial concentrates available of KOH in 50 to 65% concentration. Initial tests indicate that the test will work when 50% KOH is added to the urine and then the aluminum metal is added to initiate the color-forming gender-indicating reaction. The colors that are the end point of the test are essentially the same. The use of the liquid form of the alkali lends itself to automatic dispensing of this component and thus to the ease of automation of the test itself.

The kit aspects of this invention comprise a reaction container, a supply of the gender-indication composition, preferably premixed and subdivided into test units. For use by the general public, a color-standard chart should be included in the kit. The chart is not needed by professionals in the laboratory setting who rapidly become accustomed to the indicating colors resulting from the test.

We claim:

1. A method for the determination of the gender of the unborn child which comprises the steps of:
    (a) contacting a sample of the urine from a woman pregnant with the unborn child with a gender-indicating composition;
    (b) initiating a chemical reaction between said urine and said composition;
    (c) comparing the color developed in the reaction solution as a result of said reaction with standards indicating the gender of said unborn child;
    said urine sample being obtained from said pregnant woman during or after the 20th week of the pregnancy; and
    said gender-indicating composition comprising an alkali hydroxide and metallic aluminum in 10:1 to 2:1 proportion by weight;
    said contacting proportions of said composition to urine being from about 1:1 to about 1:6, weight to volume; said initiation of reaction being caused by the exothermic nature of the reaction;
    said color standards for gender determination comprising shades of tan which indicate a female child and shades of brown indicating a male child.

2. The method according to claim 1 wherein said urine sample is obtained from the first voiding of the day.

3. The method according to claim 1 wherein said urine sample is obtained after at least the 24th week of the pregnancy.

4. The method according to claim 1 wherein the components of said gender indicating composition are added to said urine separately but at about the same time to initiate said reaction.

5. The method according to claim 1 wherein the ratios of said total composition to said urine is about 1:2.

6. A gender-indicating composition for use in the method of claim 1 for the determination of the gender of an unborn child which comprises a subdivided portion of a mixture of alkali hydroxide and metallic aluminum, said portion consisting of an amount sufficient to react with said sample and to yield a brown or tan colored solution, said color indicating the gender of said unborn child.

7. The method according to claim 1 wherein said gender-indicating composition comprises sodium or potassium hydroxide particles or mixtures thereof as the alkali hydroxide, and said aluminum metal is in the form of fine shot, ribbon particles or turnings.

8. The method according to claim 7 wherein the ratio of said hydroxide component to said metal is about 3:1.

9. A kit for the determination of the gender of an unborn child by reacting with the urine of a pregnant woman, pregnant with said child, which comprises:
(a) kit means enclosing:
(b) a reaction vessel
(c) a portion of a gender-indicating composition
(d) a color standard for comparison;
said reaction vessel having a sufficient capacity to accept a sample of the urine from a pregnant woman and to confine the liquid reactants during the reaction of the urine with the gender-indicating composition; said gender-indicating composition comprising an alkali hydroxide and metallic aluminum, both in particulate form, and said composition portion being an amount sufficient for reacting with the urine and forming a tan or brown solution; said color standard in chart or sample form for use as a comparison standard with said colored solution and having tan standards for female indication and brown standards for male indication.

* * * * *